(12) United States Patent
Mitchell et al.

(10) Patent No.: US 11,311,212 B2
(45) Date of Patent: Apr. 26, 2022

(54) GUARD RINGS FOR ON-BODY ANALYTE SENSORS

(71) Applicant: Abbott Diabetes Care Inc., Alameda, CA (US)

(72) Inventors: Steven T. Mitchell, Pleasant Hill, CA (US); Frank David Fujimoto, Fremont, CA (US); Hyun Brian Cho, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 297 days.

(21) Appl. No.: 16/205,913

(22) Filed: Nov. 30, 2018

(65) Prior Publication Data

US 2019/0167167 A1 Jun. 6, 2019

Related U.S. Application Data

(60) Provisional application No. 62/594,744, filed on Dec. 5, 2017.

(51) Int. Cl.
*A61B 5/00* (2006.01)
*A61B 5/145* (2006.01)

(52) U.S. Cl.
CPC ...... *A61B 5/14503* (2013.01); *A61B 5/14546* (2013.01); *A61B 5/683* (2013.01); *A61B 5/6833* (2013.01); *A61B 5/6849* (2013.01); *A61B 5/145* (2013.01); *A61B 5/14532* (2013.01); *A61B 2560/0412* (2013.01); *A61B 2560/0443* (2013.01); *A61B 2562/00* (2013.01);

(Continued)

(58) Field of Classification Search
CPC ............ A61B 5/6833; A61B 2562/164; A61B 2562/146; A61B 2562/02; A61B 5/145; A61B 2560/0412
See application file for complete search history.

(56) References Cited

U.S. PATENT DOCUMENTS 6,129,666 A * 10/2000 DeLuca ................. A61B 5/296
600/372
2011/0060196 A1* 3/2011 Stafford ............... A61B 5/6833
600/309

(Continued)

OTHER PUBLICATIONS

ISR/WO for related PCT/US2018/063290 dated Feb. 14, 2019.

*Primary Examiner* — Christian Jang
(74) *Attorney, Agent, or Firm* — Sterne, Kessler, Goldstein & Fox P.L.L.C.

(57) ABSTRACT

On-body analyte sensors may be designed for extended wear to provide ongoing measurement of physiological analyte levels. However, on-body analyte sensors may be susceptible to damage or dislodgment during wear due to routine interactions that occur with one's surroundings. Guard rings may be adapted to protect on-body analyte sensors from such interactions. Guard rings may comprise an annular body comprising an inner perimeter face, an outer perimeter face, a top edge, and a bottom face adapted for contacting a tissue surface. The inner perimeter face is shaped to circumferentially surround a sensor housing of an on-body analyte sensor. At least a portion of the outer perimeter face defines a chamfered surface extending between the top face and the bottom face. Adhesive pads or strips may further be engaged with the guard rings and aid in securing the guard rings to a surface, such as skin.

17 Claims, 8 Drawing Sheets

(52) U.S. Cl.
CPC ..... *A61B 2562/02* (2013.01); *A61B 2562/146* (2013.01); *A61B 2562/164* (2013.01)

(56) References Cited

U.S. PATENT DOCUMENTS

| | | |
|---|---|---|
| 2012/0190941 A1 | 7/2012 | Donnay et al. |
| 2013/0245415 A1 | 9/2013 | Kumar et al. |
| 2016/0022179 A1* | 1/2016 | Di Resta .............. A61B 5/6832 600/316 |
| 2016/0331283 A1 | 11/2016 | Rao et al. |

* cited by examiner

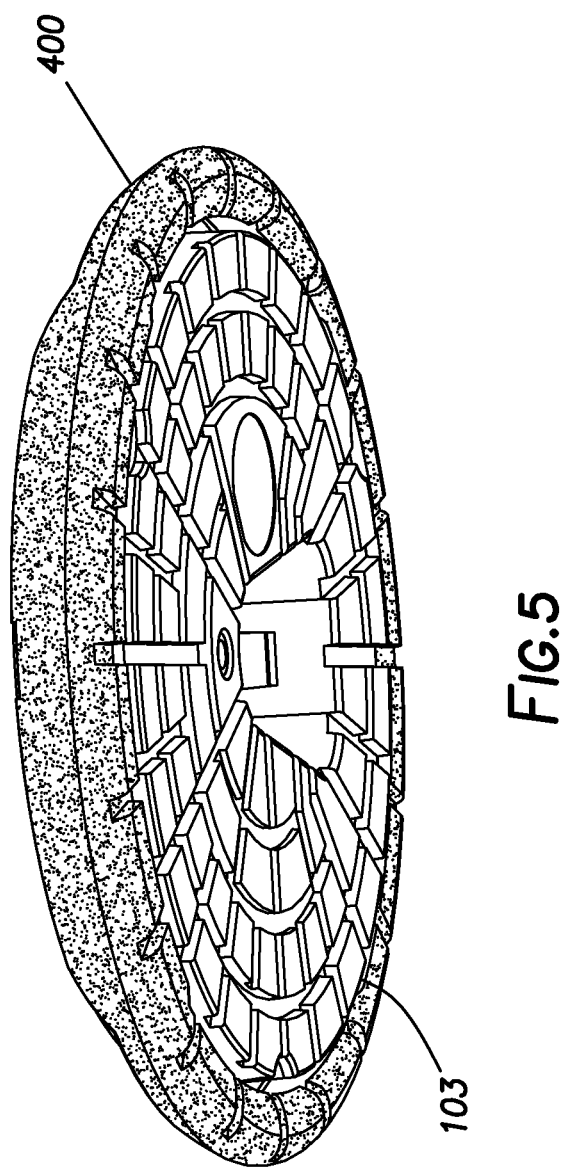

GUARD RINGS FOR ON-BODY ANALYTE SENSORS

CROSS-REFERENCE TO RELATED APPLICATIONS

This application claims priority to U.S. provisional application 62/594,744 filed Dec. 5, 2017.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health. Deviation from normal analyte levels can be indicative of a number of physiological conditions. In diabetic individuals, for example, detection of abnormal glucose levels can be essential for maintaining good health. By monitoring glucose levels with sufficient regularity, a diabetic individual may be able to take corrective action (e.g., by injecting insulin to lower glucose levels or by eating to raise glucose levels) before significant physiological harm occurs. Other analytes subject to physiological dysregulation may be similarly desirable to monitor in order to maintain good health.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain implanted within a tissue of an individual, such as dermally, subcutaneously or intravenously, through which analyses may take place in vivo. Implanted sensors may collect analyte data continuously or sporadically, depending on an individual's particular health needs.

Although the entirety of a sensor may be implanted within an individual (e.g., surgically), it is more common for primarily the active portion of the sensor to be implanted internally (e.g., through a skin penetration), with one or more additional sensor components remaining external to the individual's body. In many instances, sensors suitable for measuring analyte levels in vivo may extend from a sensor housing that is designed to be worn "on-body" for extended periods of time, such as on the skin. Such on-body analyte sensors may be especially desirable, since they often may be applied directly by a wearer, rather than relying on a medical professional to perform an invasive sensor implantation procedure.

Despite the desirability of on-body analyte sensors, their use is not without challenges. One issue associated with on-body analyte sensors is that they may be subject to damage or displacement during routine activities of a wearer. For example, bumping or catching an edge of an on-body analyte sensor upon a surrounding object may provide sufficient force to overcome adhesive bonding forces securing the sensor housing to the wearer's skin, thereby dislodging the implanted sensor from its desired internal location or even completely removing the sensor from a wearer (pullout). Any number of objects may detrimentally interact with an on-body analyte sensor in this manner, such as door frames, walls, desks, clothing, hair, and the like. While a damaged or displaced on-body analyte sensor may be replaced, if necessary, this action may represent an undesirable cost and nuisance for a wearer. In addition, the uncontrolled removal of an on-body analyte sensor may be more painful for a wearer than would otherwise be experienced during planned sensor removal.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 5 shows a perspective view of a sensor housing circumferentially surrounded by a guard ring.

DETAILED DESCRIPTION

Figure 1:
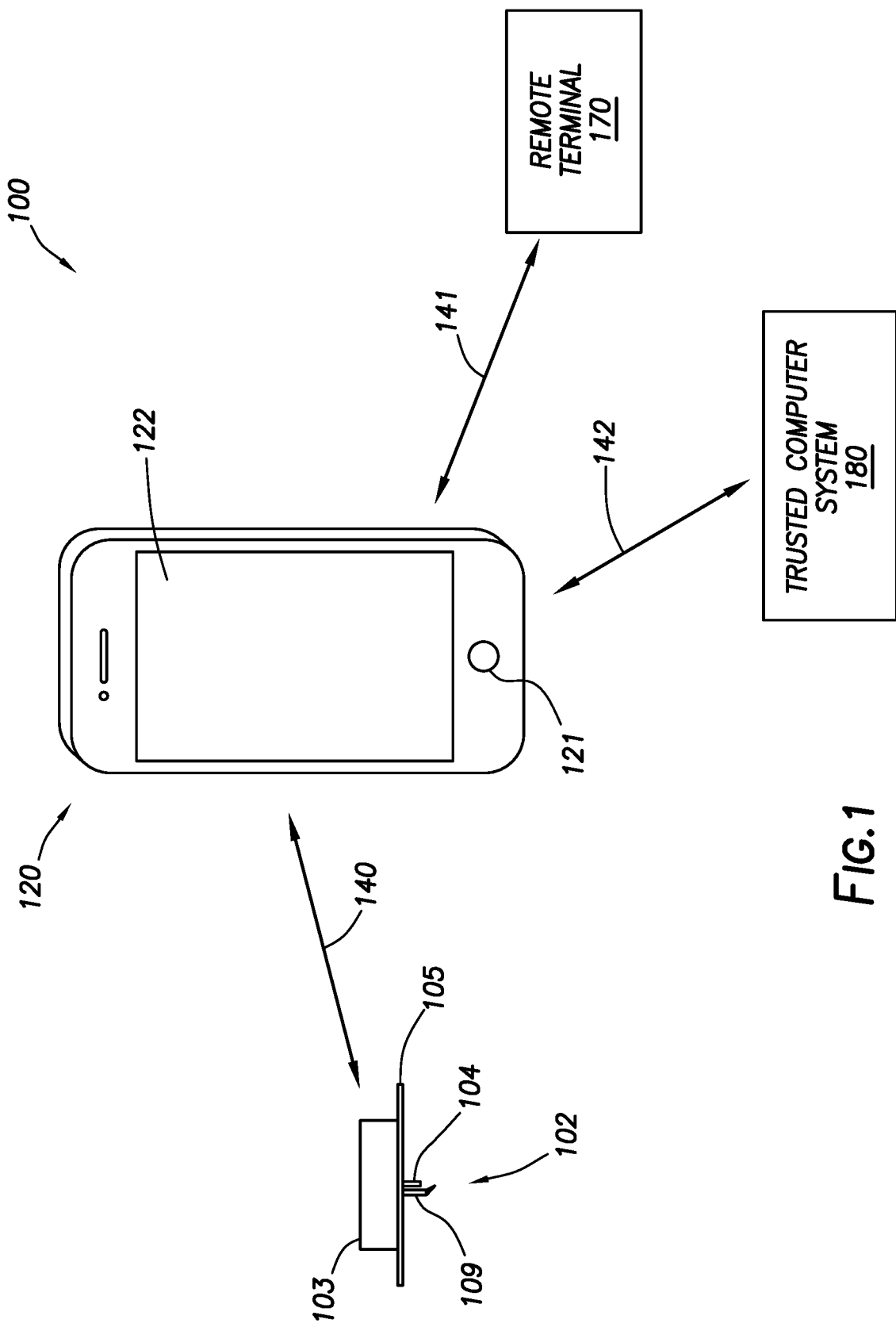
FIG. 1 shows a diagram of an illustrative in vivo analyte monitoring system that may incorporate one or more features of the present disclosure.

The present disclosure generally describes on-body analyte sensor systems and sensing techniques and, more specifically, guard rings designed to protect an on-body analyte sensor during wear.

As discussed above, on-body analyte sensors may provide a number of advantages when assaying physiological levels of one or more analytes. However, one challenge associated with the use of on-body analyte sensors is that they may be subject to damage and/or displacement, including unwanted sensor pullout, during routine activities of a wearer. Sensor displacement can be undesirable for a number of reasons, among which include inaccurate measurement of analyte levels, pain for a wearer, increased analyte measurement costs, and the need for sensor replacement.

The present inventors identified that the abrupt transition in profile height between the smooth surface of the skin and a sensor housing disposed on the skin may provide a ready location for provoking unwanted sensor displacement or dislodgment. Specifically, the outer perimeter of the sensor housing may contact or catch upon various surrounding objects or surfaces that a wearer routinely encounters during daily activities. These interactions may occur with sufficient force to dislodge the sensor housing from the skin by exceeding an adhesive bonding force otherwise tending to hold the sensor housing in place.

Accordingly, the present inventors developed various guard rings adapted for use in conjunction with on-body analyte sensors that may lessen the opportunity for sensor damage and/or displacement to occur. Specifically, the guard rings disclosed herein have an annular body and are configured to circumferentially surround the sensor housing of an on-body analyte sensor, such that the guard rings bear the brunt of the various forces encountered during routine interactions with one's surroundings, rather than the full force of such interactions being experienced by the sensor housing itself. As such, the guard rings may aid in protecting the sensor housing from damage and/or displacement.

More specifically, the guard rings of the present disclosure are configured to aid in deflecting forces associated with incidental interactions away from the sensor housing itself. To promote such force deflection, the guard rings disclosed herein may contain a chamfered (sloped or rounded sloped) outer perimeter face that promotes a glancing blow with surrounding objects and surfaces, rather than allowing the full interaction force to be borne by the guard ring and/or the sensor housing circumferentially surrounded by the guard ring. In addition, the guard rings may comprise one or more tapered and/or rounded surfaces or edges that further lessen the likelihood for detrimental interactions with surrounding objects.

While the guard rings are intended to remain attached to a tissue surface while deflecting incidental forces from deleteriously affecting a sensor housing, the guard rings may detach from the tissue surface if sufficient force is applied. Guard ring detachment, if it occurs, may take place without sensor detachment or displacement, in which case a new guard ring may be simply applied without implanting a new sensor. Ideally, the guard rings may remain attached to a tissue surface without becoming detached during incidental contact. As a further advantage, because the guard rings are replaceable, they may provide interchangeable ornamentation to the sensor housing, according to some embodiments. For example, the guard rings may be any of a variety of colors and incorporate one or more artistic designs or patterns thereon, which can allow customization to suit a given wearer's preferences.

The guard rings may be at least partially held in place through interaction with at least a portion of an adhesive layer holding the sensor housing in place (i.e., a portion of an adhesive layer circumferentially surrounding the outer perimeter of the sensor housing). Alternately, the guard rings may incorporate an independent adhesive thereon to promote adhesive bonding to a tissue surface.

Advantageously, the guard rings of the present disclosure may be further adapted to engage with one or more adhesive pads or strips that may aid in securing the guard rings to a tissue surface more securely, such as upon a wearer's skin. Numerous configurations may be suitable for incorporating an adhesive pad or strip upon, within, or in engagement with the guard rings of the present disclosure, as discussed further herein. Because the guard rings of the present disclosure may incorporate their own adhesive pad or strip, the guard rings may be replaced independently of the sensor housing, if necessary, should the guard rings become dislodged during use. Moreover, the adhesive pad or strip may further independently secure the guard rings in place when the adhesive layer associated with the sensor housing "wears out" (e.g., through debris accumulation on the adhesive layer portion not covered by the sensor body) and is no longer sufficient to maintain the guard rings securely in place by itself, even though the sensor housing itself may remain secured in place.

As a still further advantage, the guard rings of the present disclosure may be configured to discourage fluid entrapment at the interface between the guard rings and the sensor housing. Specifically, the guard rings of the present disclosure may incorporate one or more grooves on a bottom face thereof (i.e., a tissue-facing face) so as to promote fluid drainage from the sensor housing. The one or more grooves defined on the bottom face of the guard rings may extend between the inner perimeter face and the outer perimeter face to allow such fluid drainage to take place. The number and positioning of the one or more grooves may allow the rate of fluid drainage to be adjusted, in addition to tailoring the external appearance of the guard rings. According to some embodiments, the one or more grooves may be radially spaced in a uniform manner.

Moreover, and further advantageously, the one or more grooves defined upon the bottom face of the guard rings may establish fluid communication with a corresponding set of one or more grooves defined upon a bottom face (i.e., a tissue-facing face) of the sensor housing in order to promote fluid drainage. In particular, the grooves defined upon the bottom face of the sensor housing may extend to an internal receptacle configured to receive and/or contain a sensor module, where the internal receptacle is otherwise prone to retain fluid during extended user wear (e.g., due to showering, wearer perspiration, and the like). Fluid drainage from the sensor housing, as further promoted by the guard rings, can desirably protect the sensor module from damage as well as better promote tissue health where the sensor housing is adhered to a tissue surface, such as upon a wearer's skin. Tissue health may also be promoted by one or more recesses defined in the inner perimeter face of the guard rings, which may promote air circulation between the sensor housing and the guard rings while still allowing the inner perimeter face to engage the sensor housing at one or more locations. The number and patterning of the one or more grooves located upon the guard rings may be the same as or different than that of the one or more grooves located upon the sensor housing.

Before discussing particular guard ring configurations of the present disclosure, a brief overview of on-body analyte sensors will be provided so that the embodiments of the present disclosure can be better understood. On-body analyte sensors suitable for use in conjunction with the guard rings of the present disclosure may be dermal sensors, according to some embodiments. Illustrative on-body analyte sensors, particularly dermal sensors, that may be utilized in conjunction with the guard rings of the present disclosure include those described in more detail in commonly owned U.S. Pat. No. 9,668,686 and commonly owned U.S. Patent Application Publications 2012/0190941, 2016/0331283 and 2017/0196487, each of which is incorporated herein by reference in its entirety.

FIG. 1 shows a diagram of an illustrative in vivo analyte monitoring system that may incorporate one or more features of the present disclosure. As shown, analyte monitoring system 100 includes sensor device 102 and reader device 120 that are configured to communicate with one another over a local communication path or link, which may be wired or wireless, uni- or bi-directional, and encrypted or non-encrypted. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Any suitable electronic communication protocol may be used for each of the local communication paths or links.

Sensor control device 102 includes sensor housing 103, which may contain a sensor module, circuitry and a power source (not shown in FIG. 1). As shown in detail hereinafter, sensor housing 103 may contain a receptacle sized to contain the sensor module (see FIG. 3). Sensor 104 protrudes from sensor housing 103 through bottom face 105, which is configured to contact and adhere to a tissue surface, such as a wearer's skin.

Sensor 104 is adapted to be at least partially inserted into a tissue of interest, such as the dermal layer of the skin. Sensor 104 may comprise a sensor tail of sufficient length for insertion to a desired depth in a given tissue. The sensor tail may comprise the active sensing region of sensor 104. One or more analyte levels may be determined using sensor 104 and undergo communication to reader device 120, according to one or more embodiments. The analyte may be monitored in any biological fluid of interest such as dermal fluid, plasma, blood, lymph, or the like. Analytes that may be monitored are not considered to be particularly limited, provided that a suitable sensing chemistry can be identified. In certain illustrative embodiments, the analyte may be glucose.

Needle 109 may reside in proximity to sensor 104, as depicted in FIG. 1. When present, needle 109 may facilitate insertion of sensor 104 into a tissue of interest by opening an access pathway for sensor 104 to follow. For example, needle 109 may facilitate penetration of the dermis to allow implantation of sensor 104 to take place, according to one or more embodiments. In other illustrative embodiments, sensor 104 may reside within a lumen or groove of needle 109, with needle 109 similarly opening an access pathway for sensor 104. In some or other illustrative embodiments, needle 109 may be solid or hollow, beveled or non-beveled, and/or have a gauge of about 21 or smaller. It is to be recognized, however, that needle 109 may have a larger diameter (smaller gauge) if needed for particular applications. In more particular embodiments, needle 109 may be an acupuncture needle. In alternative embodiments, needle 109 may be absent, provided that sensor 104 is able to penetrate a tissue satisfactorily to establish communication with a bodily fluid of interest. Other types of introducers similar to needle 109, such as a bladed introducer, may likewise aid in promoting sensor insertion into a tissue of interest.

Reader device 120 may comprise display 122 and optional input component 121. Further optionally, input component 121 and display 122 may be combined as a single component. In some embodiments, display 122 may comprise a touch screen interface that is further configured to accept input from a user. Display 122 may show one or more pieces of information determined by sensor 104 or another sensor. Illustrative forms for showing information upon display 122 may include, but are not limited to, numerical output or graphical output (including trendlines and projected values) for one or more analyte concentrations or physiological parameters such as heart rate, body temperature, blood pressure, and the like. In further more specific embodiments, sensor 104 may be configured to detect glucose as an analyte, and display 122 may show a measured glucose value or graphical display of measured and/or projected glucose values. Input component 121, when present, may be in any suitable form for communicating with and/or operating reader device 120. In illustrative embodiments, input component 121 may comprise a button, toggle switch, actuator, touch-sensitive switch, capacitive switch, pressure-sensitive switch, jog wheel, or the like.

In certain embodiments, reader device 120 can be configured to provide signals such as output alarms, alert notifications, and the like in response to out of range values. Such signals may be visual, audible, tactile, or any combination thereof.

Figure 2:
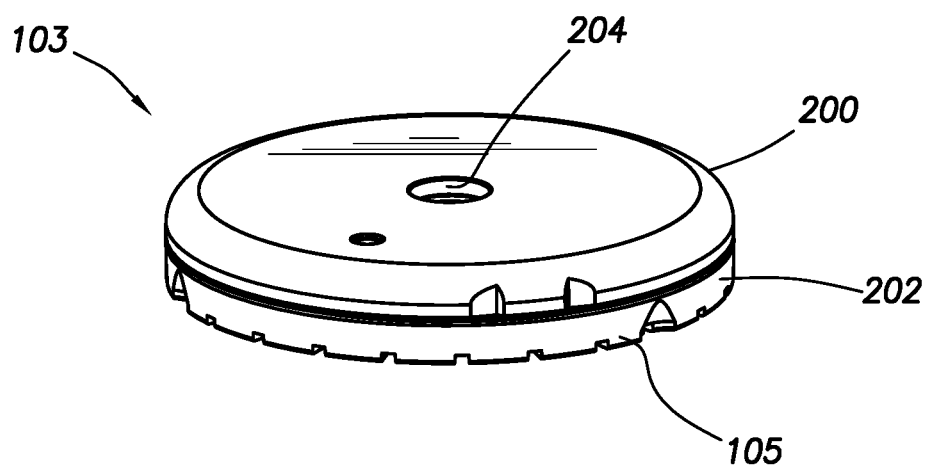
FIG. 2 shows a diagram of an illustrative sensor housing containing a distal housing portion and a proximal housing portion.

According to certain embodiments of the present disclosure, sensor housing 103 may comprise a distal housing portion and a proximal housing portion. As used herein, the term "proximal" refers to the portion of sensor housing 103 that contains bottom face 105, and which is configured to contact a tissue of interest. FIG. 2 shows a diagram of sensor housing 103 in which distal housing portion 200 and proximal housing portion 202 are coupled together, such as through snap, compression, or interference fitting, adhesive bonding, laser welding, or the like. Aperture 204 extends through distal housing portion 200 and proximal housing portion 202, and through which sensor 104 and needle 109 may project at bottom face 105. Additional details concerning bottom face 105 are provided in FIG. 3 below.

Figure 3:
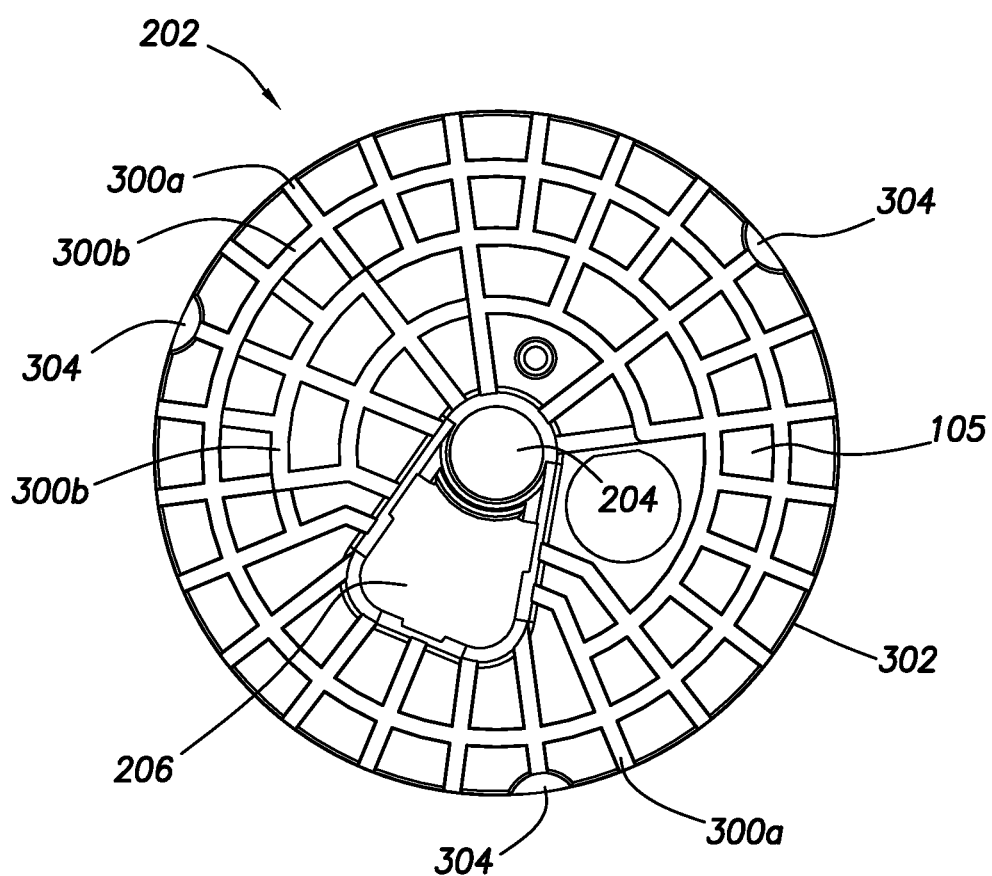
FIG. 3 shows a diagram of the bottom face of an illustrative sensor housing.

FIG. 3 shows a diagram of bottom face 105 of proximal housing portion 202 in an illustrative configuration. As shown, aperture 204 extends through bottom face 105, through which a needle may extend and then retract when deploying sensor housing 103 on a tissue surface. Also in proximity to aperture 204 is receptacle 206, within which a sensor module (not shown) may be seated and from which sensor 104 extends once sensor housing 103 is deployed on a tissue surface. Bottom face 105 may be grooved and contain a plurality of grooves. At least a portion of the grooves may be radial grooves 300a that extend from aperture 204 and/or receptacle 206 to outer perimeter face 302 of proximal housing portion 202. Radial grooves 300a may establish fluid communication between aperture 204 and/or receptacle 206 and outer perimeter face 302 and thus may promote fluid drainage. In some embodiments, at least a portion of radial grooves 300a may not extend all the way to aperture 204 and/or receptacle 206, such as if the wall thickness is not sufficiently wide to accommodate a radial groove 300a in a particular location. Moreover, in some embodiments, at least a portion of the grooves may be circumferential grooves 300b that intersect with radial grooves 300a. Also shown in FIG. 3 are recessed carrier grips 304, which may aid in releasing sensor housing 103 from a deployment tool used for attachment to a tissue surface. The deployment tool may seat a sensor module in receptacle 206 in the course of tissue attachment.

As discussed above, the outer surfaces of sensor housing 103, particularly outer perimeter face 302 and a corresponding surface on the distal housing portion, may undesirably promote sensor damage or displacement through incidental interactions with a wearer's surroundings. The guard rings of the present disclosure are adapted to address this issue by circumferentially surrounding sensor housing 103, particularly by engaging at least a portion of sensor housing 103 upon outer perimeter face 302, to lessen the effects of such incidental interactions. Although the term "circumferential" may be associated with a generally circular shape in some instances, it is to be understood that herein this term refers to any closed geometric shape having an interior space therein. As such, guard rings of the present disclosure may be generally circular in shape, but are not required to be so. In some embodiments, the guard rings may define a toroidal shape.

Accordingly, guard rings of the present disclosure may comprise an annular body comprising an inner perimeter face, an outer perimeter face, a top face, and a bottom face, in which the bottom face is adapted for contacting a tissue surface. The inner perimeter face is shaped to circumferentially surround and/or engage a sensor housing that is adapted for adhering to the tissue surface. At least a portion of the outer perimeter face may define a chamfered (sloped, rounded or rounded sloped) surface extending between the top face and the bottom face. More particularly, the chamfered surface may be such that the distance between the inner perimeter face and the outer perimeter face is smaller at the top face than is the corresponding distance at the bottom face. In more particular embodiments, the top face may comprise a top edge, which may be rounded in some embodiments. More particularly, the top edge may define an intersection between the inner perimeter face and the outer perimeter face, in which the intersection defines a rounded interface, according to some embodiments.

In some embodiments, the guard rings disclosed herein may further comprise a soft footing material upon at least a portion of the bottom face. The soft footing material may comprise a substance such as a rubber, a silicone, a polyurethane, or like compliant material. Incorporation of a compliant material upon the bottom face of the guard rings can be desirable for minimizing skin irritation and/or improving comfort for a wearer. The compliant material can be disposed upon the entire bottom face, a portion of the bottom face, or in a plurality of discontinuous locations located around the bottom face (e.g., as a plurality of feet). In addition, in some embodiments, channels may be defined in the compliant material to promote air circulation and/or fluid drainage from the sensor housing. The channels may be in fluid communication with grooves defined upon the bottom face of the sensor housing, thereby providing additional air or liquid circulation capabilities. In some or other embodiments, a compliant material can be incorporated upon the bottom face of the sensor housing as well.

The guard rings of the present disclosure will now be described in greater detail with reference to the drawings. Where feasible, and in the interest of brevity, common reference characters are used to describe elements previously described.

Figure 4A:
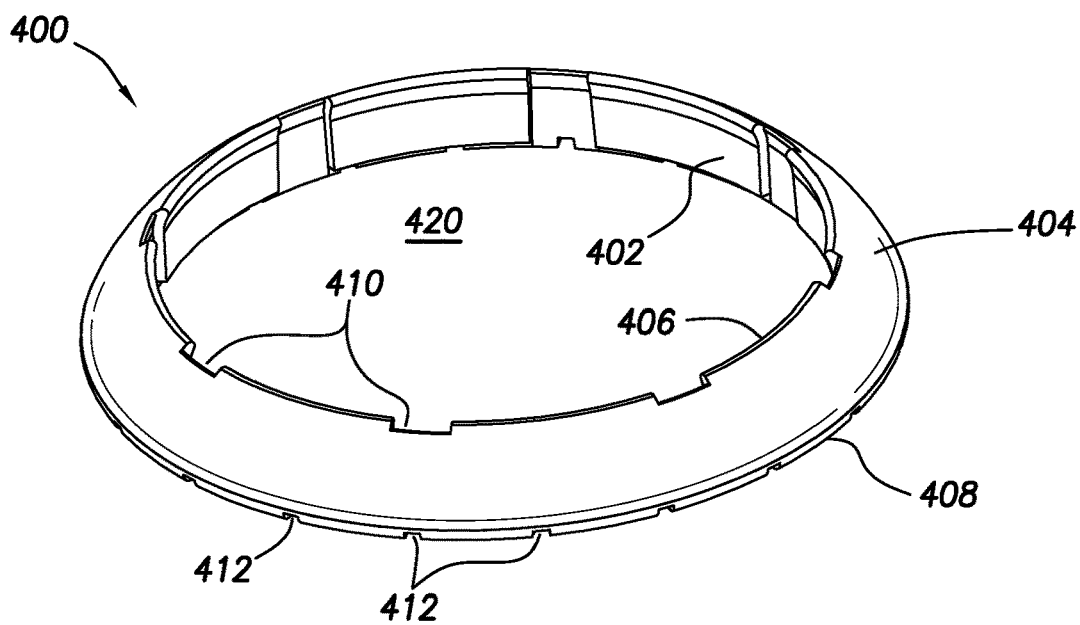
FIGS. 4A and 4B show perspective and axial views, respectively, of a first guard ring configuration of the present disclosure.
Figure 4B:
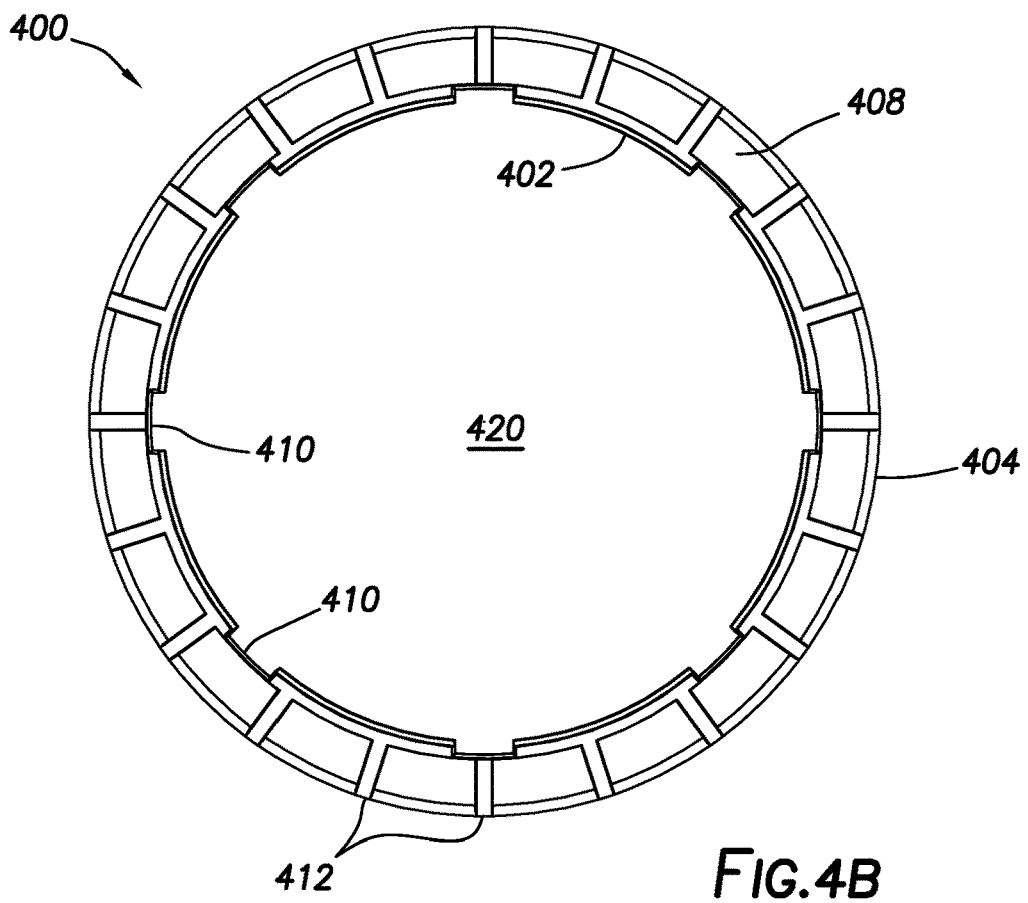

FIGS. 4A and 4B show perspective and axial views, respectively, of a first guard ring configuration of the present disclosure. Guard ring 400 includes inner perimeter face 402 and outer perimeter face 404. Outer perimeter face 404 is chamfered and extends between top face 406, which may be a top edge, and bottom face 408. The distance between inner perimeter face 402 and outer perimeter face 404 is smaller at top face 406 than is the corresponding distance at bottom face 408. That is, the slope of outer perimeter face 404 tapers from bottom face 408 to top face 406. In the depicted configuration, guard ring 400 is toroidal and interior space 420 is sized to circumferentially surround and at least partially engage a sensor housing (see FIG. 5).

Continuing with FIGS. 4A and 4B, one or more recesses 410 may be defined in inner perimeter face 402 and extend axially between top face 406 and bottom face 408. Recesses 410 may provide for air circulation in proximity to guard ring 400, particularly when guard ring 400 is in engagement or near engagement with a sensor housing (see. FIG. 5).

In addition, bottom face 408 may include one or more grooves 412 defined thereon. More specifically, grooves 412 defined on bottom face 408 may extend from inner perimeter face 402 to outer perimeter face 404. As such, grooves 412 may provide for fluid communication through bottom face 408 when guard ring 400 is disposed on a tissue surface. When guard ring 400 is engaged or nearly engaged with a sensor body (see FIG. 5), grooves 412 may be in fluid communication with one or more grooves in the sensor body (e.g., grooves 300a and 300b), thereby maintaining a complete route for fluid drainage to take place even when guard ring 400 is present. Although FIGS. 4A and 4B have shown a particular configuration for grooves 412, the number and spacing of grooves 412 is not considered to be particularly limited.

FIG. 5 shows a perspective view of sensor housing 103 circumferentially surrounded by guard ring 400. Sensor housing 103 may be affixed to a tissue surface, such as upon a wearer's skin, using an adhesive layer (not shown) concurrently applied with sensor housing 103. Suitable adhesives in the adhesive layer are not considered to be particularly limited. Guard ring 400 may be held in place around sensor housing 103 using a portion of this adhesive layer, or a separate adhesive layer associated with guard ring 400 alone (i.e., an adhesive applied to bottom face 408, such as a contact adhesive). Alternately or additionally, guard ring 400 may be held in place with an external overbandage, which may cover at least a portion of guard ring 400 and optionally sensor housing 103. As such, guard ring 400 may be adapted to engage with one or more adhesive pads or strips for securing guard ring 400 upon a tissue surface. Engagement with the adhesive pads or strips may involve placing the adhesive pads or strips over at least a portion of guard ring 400. The configuration of the adhesive pads or strips is not considered to be particularly limited.

In some or other embodiments, guard rings of the present disclosure may be adapted to receive one or more adhesive pads or strips for securing the guard ring to a surface. More particularly, in some embodiments, the adhesive pads or strips may be received within or upon at least a portion of the annular body of the guard ring. Once received, the adhesive pads or strips may be internal or external to the annular body, as described in greater detail hereinafter for various guard ring configurations. The adhesive pads or strips may be secured within or upon the annular body in a variety of ways such as, for example, adhesively, mechanically, compressively or via similar coupling techniques. In certain embodiments, a first portion of an adhesive strip may loop through an interior space of the guard ring, wrap around the bottom face or the top face of the guard ring, and adhere (i.e., adhesively bond) to the bottom face or the top face of the guard ring and/or a second portion of the adhesive strip. That is, in some embodiments, a portion of an adhesive strip may be bonded to itself in order to secure the adhesive strip to the guard ring.

Figure 6:
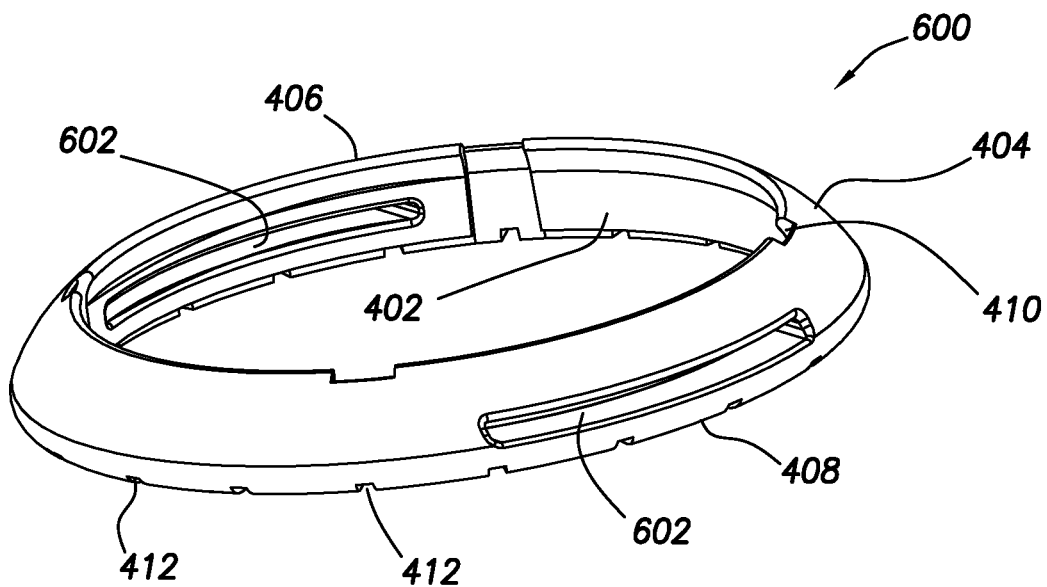
FIGS. 6 and 7 show perspective views of a second guard ring configuration of the present disclosure, in which multiple slots extend between the inner perimeter face and the outer perimeter face.
Figure 7:
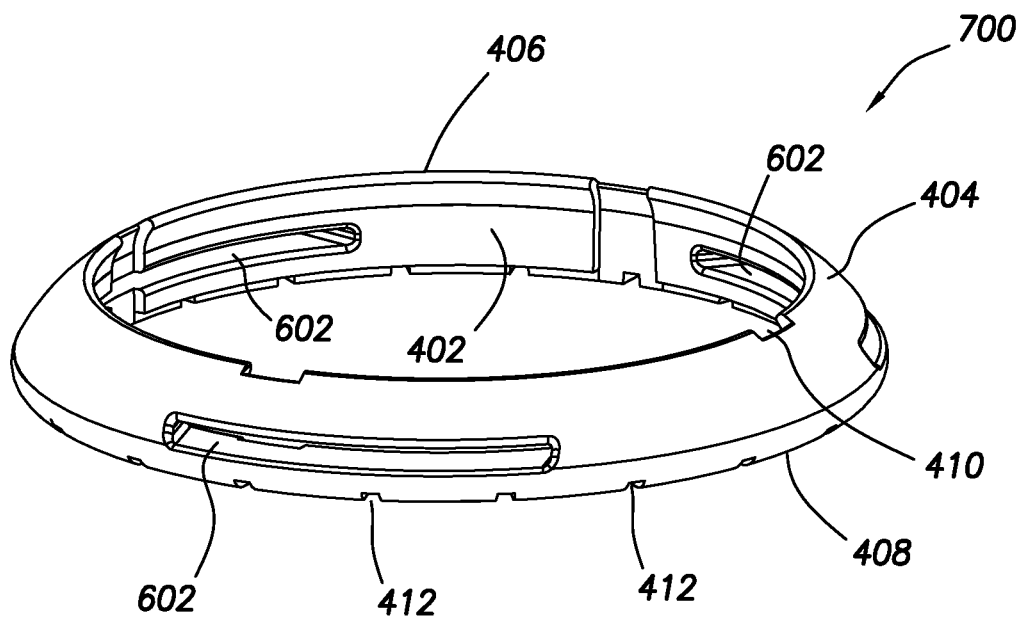

FIGS. 6 and 7 show perspective views of a second guard ring configuration of the present disclosure, in which multiple (i.e., two or more) slots 602 extend between inner perimeter face 402 and outer perimeter face 404. In the embodiment of FIG. 6, two slots 602 are disposed opposite one another and extend between inner perimeter face 402 and outer perimeter face 404. FIG. 7 differs from FIG. 6 in that three slots 602 instead of two extend between inner perimeter face 402 and outer perimeter face 404. In either case, slots 602 may be adapted to receive an adhesive strip (not shown) for purposes of securing guard ring 600 or 700 to a tissue surface, such as the skin. Slots 602 are defined in outer perimeter face 404 such that they do not intersect either top face 406 or bottom face 408.

Figure 8A:
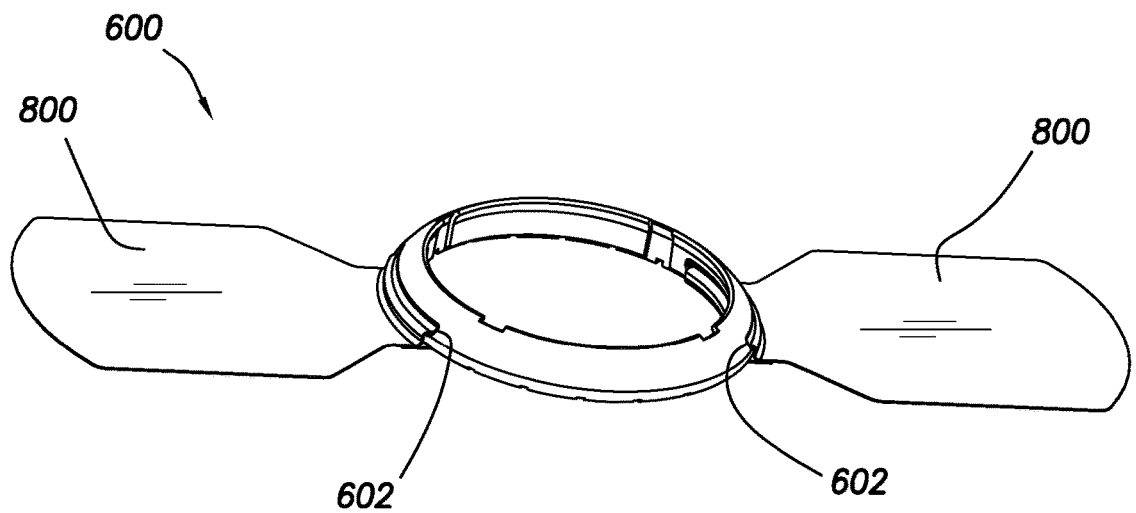
FIGS. 8A and 8B show the guard ring configuration of FIG. 6 with an adhesive strip housed in each slot.
Figure 8B:
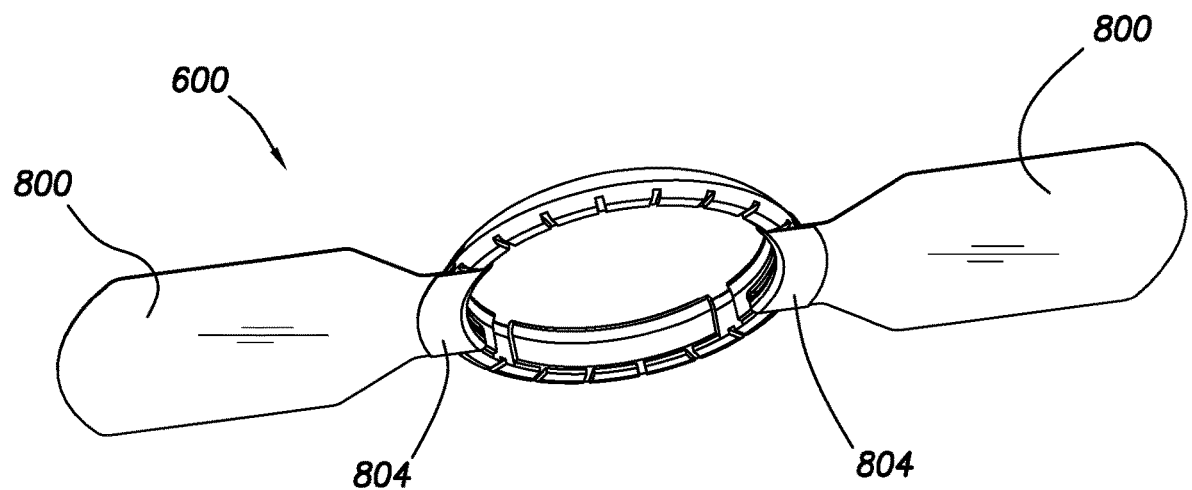

Slots 602 may be adapted for threading an adhesive strip therethrough, as shown in FIGS. 8A and 8B for guard ring 600, which incorporates adhesive strips 800 housed within each slot 602. Adhesive strips 800 may be housed and maintained in slots 602 in any feasible manner. In some embodiments, adhesive strips 800 may be folded back upon themselves, either by being folded over top face 406 or bottom face 408, to secure adhesive strips 800 within slots 602. For example, FIG. 8B illustrates how adhesive strips 800 are folded back upon themselves at bottom overfold 804 once secured in slots 602. Since the three-slot guard ring configuration of FIG. 7 contains an additional slot 602 for housing an additional adhesive strip 800, it may be better suited to maintain positioning during extended wear upon a tissue surface (i.e., by providing a greater amount of adhesive bonding force over a wider tissue contact area).

Adhesive strips may be received within or upon certain guard rings of the present disclosure without being threaded through a slot, according to some embodiments. In certain embodiments, some guard rings of the present disclosure may comprise multiple (i.e., two or more) notches defined in the top face of the guard ring, in which the notches extend between the outer perimeter face and the inner perimeter face. Whereas slots 602 of guard rings 600 and 700 in FIGS. 6 and 7 do not extend to either of top face 406 or bottom face 408, the notches described hereinabove instead remove a portion of the top face and an underlying portion of the annular body to define a suitably sized notch. Alternately, the notches may be defined during fabrication of the guard ring without removing a portion of the top face. In either case, the resulting notch may be adapted to receive an adhesive strip, as shown in more detail in FIGS. 9-12.

Figure 9:
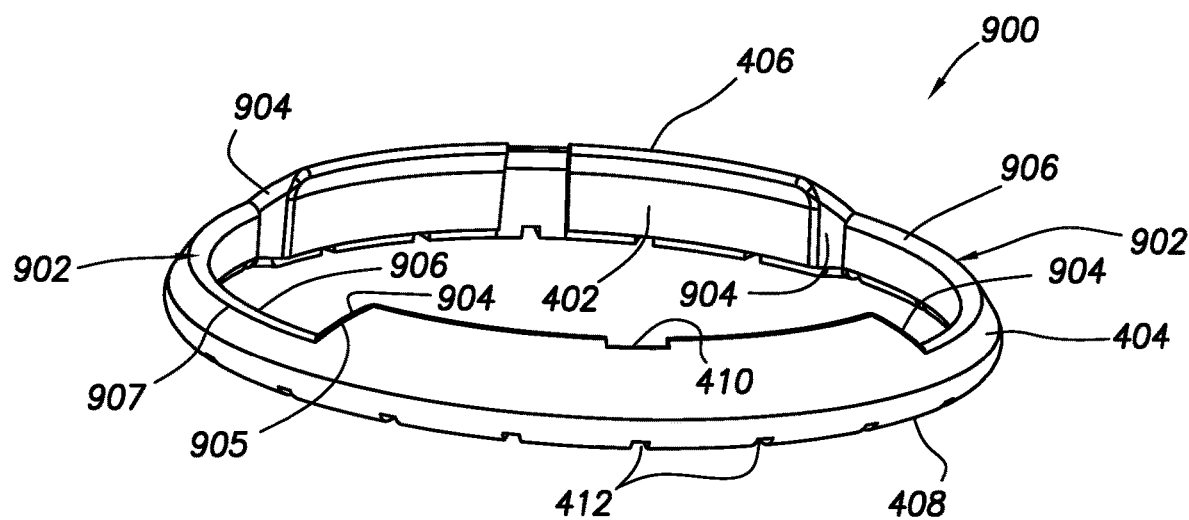
FIG. 9 shows a perspective view of a third guard ring configuration of the present disclosure, in which multiple notches are defined in the top face of the guard ring.
Figure 10:
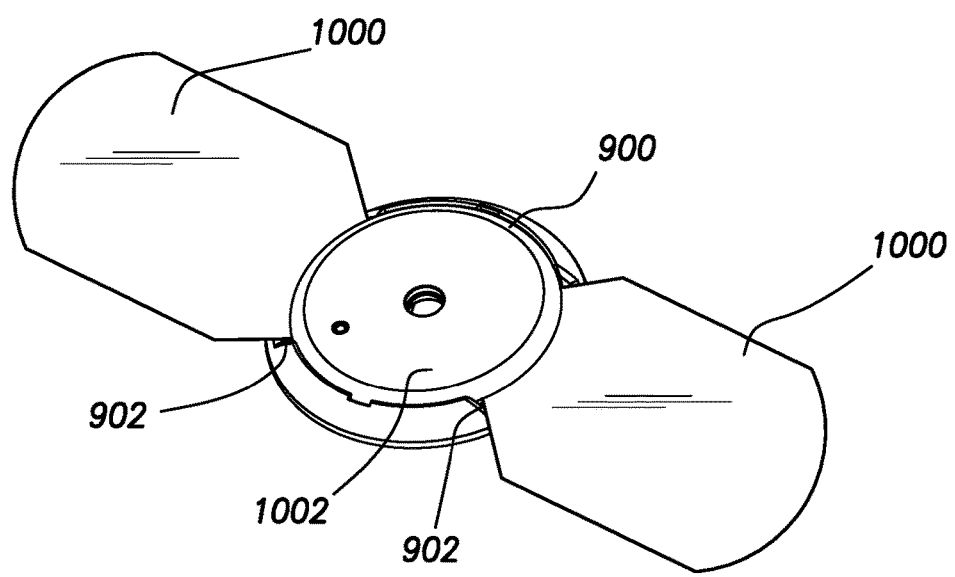
FIG. 10 shows the guard ring configuration of FIG. 9 with an adhesive strip engaged with each notch.

FIG. 9 shows a perspective view of a third guard ring configuration of the present disclosure, in which multiple notches 902 (i.e., two or more) are defined in the top face of the guard ring. Notches 902 define discontinuities in top face 406 (i.e., in a sawtooth-like pattern), which extend axially within the annular body but not all the way to bottom face 408, thereby maintaining a generally toroidal shape of the annular body. Notches 902 may be adapted for receiving an adhesive strip, as depicted in FIG. 10, which shows adhesive strips 1000 engaged within notches 902 of guard ring 900. Techniques for securing adhesive strips 1000 within notches 902 may be similar to those discussed above for securing similar adhesive strips in slots 602. Guard ring 900 may circumferentially surround sensor housing 1002, as further depicted in FIG. 10 and discussed in more detail hereinabove.

Referring again to FIG. 9, notches 902 of guard ring 900 may also include one or more tapered surfaces, which, in some embodiments, may include one or more rounded edges. Tapered surfaces and/or rounded edges may lessen the likelihood of the notches 902 or other components of guard ring 900 catching upon a surface during routine activities of a wearer. More specifically, notches 902 may include tapered sides 904, which optionally may comprise one or more rounded edges 905, and bottom surface 906, which may likewise optionally comprise rounded edge 907.

In addition, in some embodiments, the distance between inner perimeter face 402 and outer perimeter face 404 may decrease in proximity to notches 902 in guard ring 900. That is, in some embodiments, guard ring 900 may exhibit a smaller wall thickness at notches 902 than at other locations within the annular body. Lessening the wall thickness of the annular body in proximity to notches 902 can facilitate attachment of adhesive strips 1000 thereto. In other embodiments, the wall thickness of guard ring 900 may remain consistent all around the annular body, even where notches 902 are present. That is, in some embodiments, the inner diameter of guard ring 900 may remain substantially constant.

Still other notch configurations are also possible. According to some embodiments, certain guard rings of the present disclosure may further comprise an insert piece coupled to the annular body within each notch. The insert piece may be adapted to engage an adhesive strip, thereby aiding in securing the adhesive strip within the notch. In some embodiments, the insert piece may be removably coupled to the annular body within the notch, thereby allowing replacement of the adhesive strip, if needed. In other embodiments, the insert piece may be non-removable from the notch once coupled to the annular body (e.g., by adhesive bonding or a sufficiently tight interference fit). In some or other embodiments, the adhesive strip may be retained within the notch by other means in addition to the insert piece, such as adhesively, for example.

Figure 11:
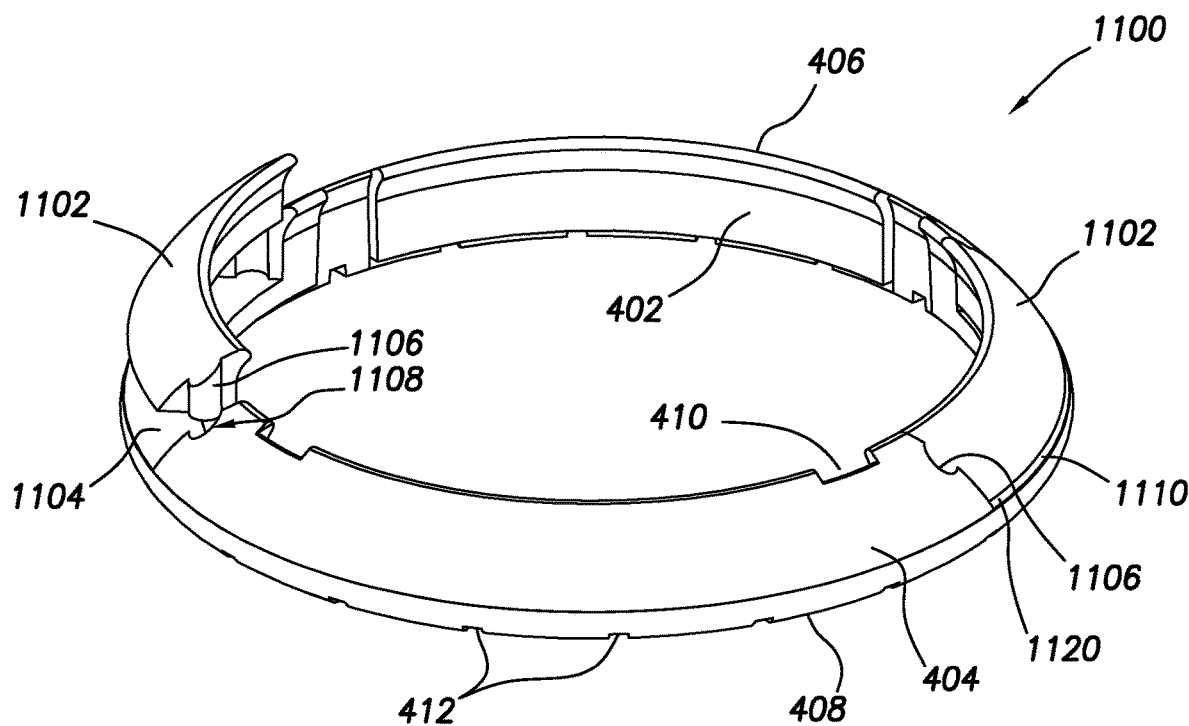
FIG. 11 shows a perspective, partially exploded view of a fourth guard ring configuration of the present disclosure, in which an insert piece is coupled to and at least partially fills each notch.
Figure 12:
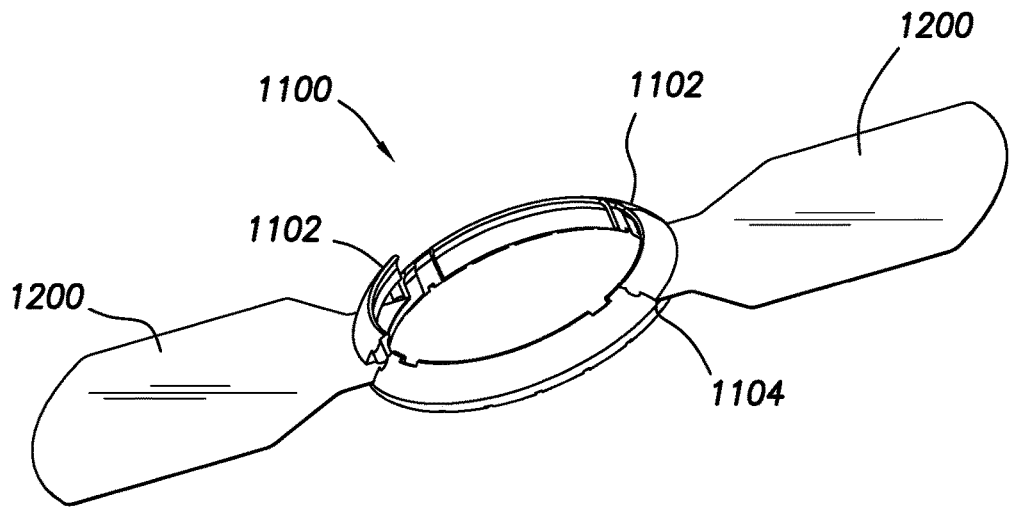
FIG. 12 shows the guard ring configuration of FIG. 11, again in partially exploded view, with an adhesive strip secured in each notch by an insert piece.

FIG. 11 shows a perspective, partially exploded view of a fourth guard ring configuration of the present disclosure, in which insert pieces 1102 are coupled to and at least partially fill notches 1104 within guard ring 1100. In the partially exploded view of FIG. 11, only one insert piece 1102 has been seated and the other notch remains unfilled. As depicted, insert pieces 1102 may contain tabs 1106 that are configured to engage with corresponding recesses 1108 defined in outer perimeter face 408. Alternately, insert pieces 1102 may contain recesses 1108 and tabs 1106 may be defined on outer perimeter face 408. Tabs 1106 and recesses 1108 define a complementary or "puzzle-piece" type connection, although other types of coupling motifs are possible. As depicted, tabs 1106 and recesses 1108 are configured to mate with one another via axial insertion of tabs 1106 into recesses 1108, but other mating orientations also reside within the scope of the present disclosure. For example, in some embodiments, tabs 1106 and recesses 1108 may be arranged such that insert pieces 1102 may be inserted radially into notches 1104 rather than axially.

According to some embodiments, insert pieces 1102 may be contiguous with inner perimeter face 402, outer perimeter face 404, and top face 406 of guard ring 1100 when inserted in notches 1104. That is, guard ring 1100 may present a smooth transition between insert piece 1102 and the annular body at these locations. Making the insert piece contiguous with the annular body at these locations may again lessen the likelihood of guard ring 1100 inadvertently catching on various surfaces during day-to-day activities of a wearer. A small gap 1120 may be present on the underside of insert piece 1102, which may be sized to receive an adhesive strip, as shown in FIG. 12, again in partially exploded view.

Once insert pieces 1102 have been inserted into notches 1104, guard ring 1100 may somewhat resemble guard ring 400 of FIGS. 4A and 4B, with the exception of gap 1120 being present at interface 1110 between insert pieces 1102 and the remainder of the annular body. Other than gap 1120 at interfaces 1110, guard ring 1100 primarily differs from guard ring 400 in its ability to receive an adhesive strip internally within the annular body. More specifically, as discussed above, adhesive strips 1200 may be received within notches 1104 and become secured in place upon seating insert pieces 1102.

In view of the foregoing, the present disclosure also describes in vivo analyte monitoring systems employing a guard ring, both of which are adapted for securement to a tissue surface. In some embodiments, such in vivo analyte monitoring systems may comprise: a sensor housing containing a sensor module, the sensor housing being adapted for adhering to a tissue surface and at least a portion of the sensor module being adapted for penetrating the tissue surface; and a guard ring circumferentially surrounding the sensor housing. The guard ring comprises an annular body comprising an inner perimeter face, an outer perimeter face, a top face and a bottom face. At least a portion of the outer perimeter face defines a chamfered surface extending between the top face and the bottom face. When disposed upon a tissue surface, at least a sensor tail of a sensor extending from the sensor module may penetrate the tissue surface, optionally further aided by a needle.

In further embodiments, the in vivo analyte monitoring systems may further comprise one or more adhesive pads or strips engaged with and/or received within the guard ring. As discussed above, the one or more adhesive pads or strips may be adapted for securing the guard ring upon a tissue surface. Any of the guard ring configurations disclosed hereinabove may be employed in the in vivo analyte monitoring systems disclosed herein, with an appropriate adhesive pad or strip being selected for complementarity with the guard ring. For example, an overbandage may be appropriate for securing guard ring 400 to a tissue surface, whereas adhesive strips integral with or secured within guard rings 600, 700, 900 or 1100 may be more appropriate for those configurations.

According to some embodiments, any of the guard rings employed with the in vivo analyte monitoring systems disclosed herein may comprise one or more grooves defined in the bottom face of the guard rings, as discussed above. The one or more grooves may extend between the inner perimeter face and the outer perimeter face of the guard rings.

In some or other embodiments, the sensor housing may also comprise one or more grooves defined in a tissue-facing surface of the sensor housing. More specifically, the sensor housing may comprise a receptacle adapted to receive the sensor module (see FIG. 3), and one or more grooves defined in the tissue-facing surface of the sensor housing. In still more specific embodiments, at least a portion of the one or more grooves on the tissue-facing surface may extend between the receptacle and an outer perimeter edge of the sensor housing. The one or more grooves on the tissue-facing surface of the sensor housing may allow fluid drainage from the receptacle to take place. The one or more grooves defined on the bottom face of the guard rings may be in fluid communication with the one or more grooves on the tissue-facing surface of the sensor housing, thereby further facilitating fluid drainage through the guard rings. That is, the guard rings of the present disclosure are configured such that they do not substantially retain fluid between the guard ring and the sensor housing that they circumferentially surround.

Methods for using the guard rings of the present disclosure are also contemplated herein. In general, the methods may comprise, applying a sensor housing to a tissue surface, and placing a guard ring around the sensor housing such that the sensor housing is circumferentially surrounded by the guard ring. The sensor housing and the guard ring may be placed upon the tissue surface at the same time or at different times, depending on the manner in which the sensor housing is applied. For example, an applicator designed for attaching the sensor housing to a tissue surface may be further adapted for attaching a guard ring, according to some embodiments. In other embodiments, a guard ring may be applied (e.g., by a wearer) after applying the sensor housing. In further embodiments, the methods may comprise replacing a guard ring, should guard ring displacement occur during the course of wearing the sensor housing. Any of the guard ring configurations disclosed herein may be employed in the course of attaching a sensor housing to a tissue surface.

Embodiments disclosed herein include:

A. Guard rings for an on-body analyte sensor. The guard rings comprise: an annular body comprising an inner perimeter face, an outer perimeter face, a top face, and a bottom face, the bottom face being adapted for contacting a tissue surface; wherein the inner perimeter face is shaped to circumferentially surround a sensor housing adapted for adhering to the tissue surface, and at least a portion of the outer perimeter face defines a chamfered surface extending between the top face and the bottom face.

B. In vivo analyte monitoring systems. The in vivo analyte monitoring systems comprise: a sensor housing containing a sensor module, the sensor housing being adapted for adhering to a tissue surface and at least a portion of the sensor module being adapted for penetrating the tissue surface; and a guard ring circumferentially surrounding the sensor housing, the guard ring comprising an annular body comprising an inner perimeter face, an outer perimeter face, a top face, and a bottom face; wherein at least a portion of the outer perimeter face defines a chamfered surface extending between the top face and the bottom face.

Each of embodiments A and B may have one or more of the following additional elements in any combination:

Element 1: wherein the guard ring is adapted to engage with one or more adhesive pads or strips for securing the guard ring upon the tissue surface.

Element 2: wherein the guard ring is adapted to receive the one or more adhesive pads or strips within at least a portion of the annular body.

Element 3: wherein the guard ring further comprises: two or more slots extending between the outer perimeter face and the inner perimeter face, each slot being adapted to receive an adhesive strip.

Element 4: wherein the guard ring further comprises: an adhesive strip housed in each slot.

Element 5: wherein the guard ring further comprises: two or more notches defined in the top face and extending between the outer perimeter face and the inner perimeter face, each notch being adapted to receive an adhesive strip.

Element 6: wherein the guard ring further comprises: an adhesive strip engaged with each notch.

Element 7: wherein the two or more notches each comprise one or more tapered surfaces.

Element 8: wherein the one or more tapered surfaces have one or more rounded edges.

Element 9: wherein the two or more notches each comprise a bottom surface having one or more rounded edges.

Element 10: wherein the guard ring further comprises: an insert piece coupled to the annular body within each notch, the insert piece being adapted to secure an adhesive strip to the notch.

Element 11: wherein the insert piece is contiguous with the inner perimeter face, the outer perimeter face, and the top face of the guard ring when inserted in the notch.

Element 12: wherein the top face is a top edge defining an intersection between the inner perimeter face and the outer perimeter face.

Element 13: wherein the top edge is rounded.

Element 14: wherein the annular body is toroidal.

Element 15: wherein the bottom face comprises one or more grooves extending between the inner perimeter face and the outer perimeter face.

Element 16: wherein the guard ring further comprises: one or more recesses defined in the inner perimeter face and extending between the top face and the bottom face.

Element 17: wherein the sensor housing comprises a receptacle adapted to receive the sensor module and one or more grooves defined in a tissue-facing surface of the sensor housing, at least a portion of the one or more grooves extending between the receptacle and an outer perimeter edge of the sensor housing.

Element 18: wherein one or more grooves are defined in the bottom face of the guard ring.

Element 19: wherein the in vivo analyte monitoring system further comprises: one or more adhesive pads or strips engaged with the guard ring, the one or more adhesive pads or strips being adapted for securing the guard ring upon the tissue surface.

By way of non-limiting example, exemplary combinations applicable to A and B include: The guard ring of A or the in vivo analyte monitoring system of B in combination with elements 1 and 2; 2 and 3; 2-4; 1, 2 and 3; 1, 2 and 5; 3 and 4; 5 and 6; 5-7; 5-8; 5 and 7; 5 and 8; 10 and 11; 1, 10 and 11; 1, 2, 10 and 11; 1, 2, 5 and 10; 1, 2, 5, 6 and 10; 1, 2 and 10; 1, 2 and 13; 1, 2, 3 and 13; 1, 2, 3 and 14; 1, 2, 5 and 13; 1, 2, 5 and 14; 1 and 15; 1, 2 and 15; 1, 2, 3 and 15; 1, 2, 5 and 15; 1, 2, 10 and 15; 12 and 15; 12, 13 and 15; 13 and 14; 15 and 16; 1, 2, 3 and 16; and 1, 2, 5 and 16.

By way of further non-limiting example, exemplary combinations applicable to B include: The in vivo analyte monitoring system of B in combination with elements 17 and 18; 17 and 19; 17-19; and 18 and 19.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A guard ring comprising:
   an annular body comprising an inner perimeter face, an outer perimeter face, a top face, and a bottom face, the bottom face being adapted for contacting a tissue surface;
   wherein the inner perimeter face is shaped to circumferentially surround a sensor housing adapted for adhering to the tissue surface, and at least a portion of the outer perimeter face defines a chamfered surface extending between the top face and the bottom face, and
   wherein when the sensor housing is adhered to the tissue surface and when the guard ring and sensor housing are engaged, the guard ring is adapted for removal and replacement independently of the sensor housing.

2. The guard ring of claim 1, wherein the guard ring is adapted to engage with one or more adhesive pads or strips for securing the guard ring upon the tissue surface.

3. The guard ring of claim 2, wherein the guard ring is adapted to receive the one or more adhesive pads or strips within at least a portion of the annular body.

4. The guard ring of claim 3, further comprising:
two or more slots extending between the outer perimeter face and the inner perimeter face, each slot being adapted to receive an adhesive strip.

5. The guard ring of claim 4, further comprising:
an adhesive strip housed in each slot.

6. The guard ring of claim 3, further comprising:
two or more notches defined in the top face and extending between the outer perimeter face and the inner perimeter face, each notch being adapted to receive an adhesive strip.

7. The guard ring of claim 6, further comprising:
an adhesive strip engaged with each notch.

8. The guard ring of claim 6, wherein the two or more notches each comprise one or more tapered surfaces.

9. The guard ring of claim 8, wherein the one or more tapered surfaces have one or more rounded edges.

10. The guard ring of claim 6, wherein the two or more notches each comprise a bottom surface having one or more rounded edges.

11. The guard ring of claim 6, further comprising:
an insert piece coupled to the annular body within each notch, the insert piece being adapted to secure an adhesive strip to the notch.

12. The guard ring of claim 11, wherein the insert piece is contiguous with the inner perimeter face, the outer perimeter face, and the top face of the guard ring when inserted in the notch.

13. The guard ring of claim 11, further comprising:
an adhesive strip engaged with each notch.

14. The guard ring of claim 1, wherein the top face is a top edge defining an intersection between the inner perimeter face and the outer perimeter face.

15. The guard ring of claim 14, wherein the top edge is rounded.

16. The guard ring of claim 1, wherein the bottom face comprises one or more grooves extending between the inner perimeter face and the outer perimeter face.

17. The guard ring of claim 1, further comprising:
one or more recesses defined in the inner perimeter face and extending between the top face and the bottom face.

* * * * *